United States Patent [19]

Han et al.

[11] Patent Number: 5,105,044
[45] Date of Patent: * Apr. 14, 1992

[54] CATALYST AND PROCESS FOR UPGRADING METHANE TO HIGHER HYDROCARBONS

[75] Inventors: Scott Han, Lawrenceville, N.J.; Lorenzo C. DeCaul, Chester, Pa.; Robert E. Palermo, Bloomfield, N.J.; Dennis E. Walsh, Richboro, Pa.

[73] Assignee: Mobil Oil Corp., Fairfax, Va.

[*] Notice: The portion of the term of this patent subsequent to Jun. 18, 2008 has been disclaimed.

[21] Appl. No.: 597,220

[22] Filed: Oct. 15, 1990

Related U.S. Application Data

[63] Continuation-in-part of Ser. No. 459,221, Dec. 29, 1989, Pat. No. 5,025,109.

[51] Int. Cl.$^5$ .............................................. C07C 2/00
[52] U.S. Cl. ................................ 585/500; 585/943; 585/654; 585/656; 585/659; 585/661; 585/662; 585/663; 585/700; 585/400; 585/417
[58] Field of Search ............... 585/943, 500, 654, 656, 585/659, 661, 662, 663, 700, 400, 417

[56] References Cited

U.S. PATENT DOCUMENTS

| | | | |
|---|---|---|---|
| 4,172,810 | 10/1979 | Mitchell et al. | 585/943 |
| 4,443,649 | 4/1984 | Jones et al. | 585/500 |
| 4,695,668 | 9/1987 | Velenyi | 585/943 |
| 4,721,828 | 1/1988 | Withers | 585/943 |
| 4,769,508 | 9/1988 | Gastinger et al. | 585/943 |
| 4,777,313 | 10/1988 | Sofranko et al. | 585/500 |
| 4,886,931 | 12/1989 | Bartek et al. | 585/943 |
| 4,950,827 | 8/1990 | Erekson et al. | 585/943 |
| 4,950,836 | 8/1990 | Kimble et al. | 585/943 |
| 4,962,261 | 10/1990 | Abrevaya et al. | 585/500 |

*Primary Examiner*—Patrick P. Garvin
*Assistant Examiner*—E. D. Irzinski
*Attorney, Agent, or Firm*—Alexander J. McKillop; Charles J. Speciale; Edward F. Kenehan, Jr.

[57] ABSTRACT

There is provided a catalyst and a process for the direct partial oxidation of methane with oxygen, whereby hydrocarbons having at least two carbon atoms are produced. The catalyst used in this reaction is a spinel oxide, such as $MgMn_2O_4$ or $CaMn_2O_4$, modified with an alkali metal, such as Li or Na.

10 Claims, No Drawings

CATALYST AND PROCESS FOR UPGRADING METHANE TO HIGHER HYDROCARBONS

CROSS-REFERENCE TO RELATED APPLICATION

This application is a continuation-in-part of copending U.S. application Ser. No. 459,221, filed Dec. 29, 1989, now U.S. Pat. No. 5,025,109 the entire disclosure of which is expressly incorporated herein by reference.

BACKGROUND

There is provided a catalyst and a process for the direct partial oxidation of methane with oxygen, whereby hydrocarbons having at least two carbon atoms are produced. The catalyst used in this reaction comprises a spinel oxide, such as $MgMn_2O_4$ or $CaMn_2O_4$, modified with an alkali metal, such as lithium or sodium.

Natural gas is an abundant fossil fuel resource. Recent estimates places worldwide natural gas reserves at about $35 \times 10^{14}$ standard cubic feet corresponding to the energy equivalent of about 637 billion barrels of oil.

The composition of natural gas at the wellhead varies but the major hydrocarbon present is methane. For example the methane content of natural gas may vary within the range of from about 40 to 95 vol %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_{3+}$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Processed natural gas, consisting essentially of methane, (typically 85–95 volume percent) may be directly used as clean burning gaseous fuel for industrial heat and power plants, for production of electricity, and to fire kilns in the cement and steel industries. It is also useful as a chemicals feedstock, but large-scale use for this purpose is largely limited to conversion to synthesis gas which in turn is used for the manufacture of methanol and ammonia. It is notable that for the foregoing uses no significant refining is required except for those instances in which the wellhead-produced gas is sour, i.e., it contains excessive amounts of hydrogen sulfide. Natural gas, however, has essentially no value as a portable fuel at the present time. In liquid form, it has a density of 0.415 and a boiling point of minus 162° C. Thus, it is not readily adaptable to transport as a liquid except for marine transport in very large tanks with a low surface to volume ratio, in which unique instance the cargo itself acts as refrigerant, and the volatilized methane serves as fuel to power the transport vessel. Large-scale use of natural gas often requires a sophisticated and extensive pipeline system.

A significant portion of the known natural gas reserves is associated with fields found in remote, difficulty accessible regions. For many of these remote fields, pipelining to bring the gas to potential users is not economically feasible.

Indirectly converting methane to methanol by steam-reforming to produce synthesis gas as a first step, followed by catalytic synthesis of methanol is a well-known process. The Mobil Oil Process, developed in the last decade provides an effective means for catalytically converting methanol to gasoline, e.g. as described in U.S. Pat. No. 3,894,107 to Butter et al. Although the market for gasoline is huge compared with the market for methanol, and although this process is currently used in New Zealand, it is complex and its viability appears to be limited to situations in which the cost for supplying an alternate source of gasoline is exceptionally high. There evidently remains a need for other ways to convert natural gas to higher valued and/or more readily transportable products.

One approach to utilizing the methane in natural gas is to convert it to higher hydrocarbons (e.g. $C_2H_6$; $C_2H_4$; $C_3H_8$; $C_3H_6$ ...); these have greater value for use in the manufacture of chemicals or liquid fuels. For example, conversion of methane to ethane or ethylene, followed by reaction over a zeolite catalyst can provide a route to gasoline production that entails fewer steps than the indirect route via methanol synthesis described above. Unfortunately, the thermal conversion of methane to ethane is a thermodynamically unfavorable process ($\Delta G \cdot \geq +8$ kcal/mol $CH_4$) throughout the range from 300–1500K. The upgrading reactions explored here are oxidative conversions of methane to higher hydrocarbons, as exemplified in the following equations.

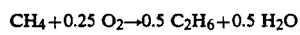

$$CH_4 + 0.25\ O_2 \rightarrow 0.5\ C_2H_6 + 0.5\ H_2O$$

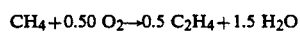

$$CH_4 + 0.50\ O_2 \rightarrow 0.5\ C_2H_4 + 1.5\ H_2O$$

Analogous reactions include those converting methane to $C_3$, $C_4$, ... and higher hydrocarbons. These oxidation processes have very favorable free energy changes ($\Delta G \cdot < -19$ kcal/mol $CH_4$) throughout the temperature range of 300–1000K. The oxidation reactions are commonly performed in the presence of a catalyst. The use of the catalyst allows the reaction to occur under conditions where there is essentially no thermal reaction between methane and oxygen. The catalyst can also favorably influence the selectivity of the oxidation reaction to minimize the extent of over-oxidation to CO and $CO_2$.

While numerous catalysts have been employed in this reaction, there has not been any report regarding application of spinels as catalysts to upgrade methane/natural gas in this manner. The application described here likewise stands in contrast to references citing spinels as catalysts for total combustion (Happel, J.; Hnatow, M.; Bajars, L. "Base Metal Oxide Catalysts"; Marcel Dekker, Inc.: New York, NY, 1977) or as catalysts for oxidative chlorination of methane to methylchloride (Vlasenko, V. M., et al, Kinet. Katal, 1984, 22, 28).

SUMMARY

There is provided a process for synthesizing one or more hydrocarbons having at least two carbon atoms by the direct partial oxidation of methane, said process comprising contacting a mixture of methane and oxygen with a catalyst under sufficient conversion conditions, said catalyst comprising a spinel oxide modified with an alkali metal. After this conversion, the one or more hydrocarbons having at least two carbon atoms may be recovered. The catalyst of this process is also provided herein.

EMBODIMENTS

Methane is converted to higher hydrocarbons such as ethane and ethylene via reaction with oxygen over a catalyst comprised of a metal oxide having the spinel structure with a portion of alkali metal as a modifier. The presence of alkali-modifier results in an improved selectivity for the production of higher hydrocarbons vs the unmodified spinel. The spinel has the general formula $AB_2O_4$; examples include manganese-based spinels such as $AMn_2O_4$ or $MnB_2O_4$. The alkali metal used as a modifier may be Li, Na, K, Rb, or Cs. The alkali metal may be combined with or incorporated into the catalyst with the spinel by a variety of methods such as impregnation or precipitation, or by inclusion during the synthesis of the spinel. The modified material may have a crystal structure analogous to the unmodified starting spinel, but with portions of alkali metal ions incorporated into the crystal lattice of the spinel.

Spinel oxides are a known class of materials which may be naturally occurring or synthetic. These spinels are structural type of oxide having the formula $AB_2O_4$ where A and B may be the same elements or different elements; the labels A and B distinguish the lattice sites occupied by the metal ions. The valencies of A and B satisfy the charge balance of the formula, i.e. the sums of charges on A plus 2B equals 8+. Examples of A are Li, Mg, Na, Ca, V, Mo, Mn, Fe, Co, Ni, Cu, Zn, Ge, Cd and Sn and examples of B are Na, Al, Ti, V, Cr, Mn, Fe, Co, Ni, Ga, Ge, Zn, Rh, Ag and In. Particular examples of spinel oxides, which are useful in the present process, are those where either A or B is Mn. Particular species of such spinel oxides include $MgMn_2O_4$ and $CaMn_2O_4$. Spinel oxides have a structure similar to ferrites.

In the practice of the present invention, it is preferred to use a dual flow system, i.e., a system in which the methane and the oxygen or air are kept separate until mixed just prior to being introduced into the reactor. However, if desired, the oxygen and methane may be premixed and stored together prior to the reaction. The preferred dual flow system minimizes the risk of fire or explosion.

The methane feed for the present reaction may be provided by pure methane or by a methane containing gas, e.g., containing at least 50 percent by weight methane. An example of a methane feed is natural gas.

Air may be used instead of oxygen; inert diluents such as nitrogen, argon, helium, steam or $CO_2$ may also be cofed. The gas comprising the methane may be derived from processed natural gas. In the system, the amount of oxygen is controlled so as to prepare a reaction mixture where the volume ratio of methane to oxygen is within the range of 0.1-100:1, more preferably in the range of 1-50:1, even more preferably in the range of 1-10:1. The operating pressure for the reactants (methane and oxygen) may be within the range of 0.1 to 30 atmospheres, preferably within the range of 0.5-5 atm. The flow rate of the methane feed gas over the catalyst may be expressed as the methane weight flow rate divided by the weight of catalyst, giving the Weight Hourly Space Velocity (WHSV) in units of $hr^{-1}$. Preferred WHSV is within the range of 0.01-150 $hr^{-1}$, e.g., 0.1-50 $hr^{-1}$. The WHSV may be chosen to maximize the selectivity to higher hydrocarbon products, or to maximize the conversion of either methane or oxygen reactant.

The temperature in the reaction zone maybe from about 300° C. to 1200° C., preferably about 500° C. to 1000° C., more preferably from 600° C. to 900° C.

The alkali-modified spinel oxides may contain from about 0.01 wt. % to about 10 wt. % of alkali metal based upon the total weight of the alkali metal plus spinel oxide.

EXAMPLE

The following terms are defined. Methane conversion: the percentage of carbon atoms in the feed converted to other products. $C_{2+}$ selectivity: percentage of carbon atoms derived from converted methane which ends up as $C_2H_6$, $C_2H_4$, $C_3H_8$, $C_3H_6$, . . . (i.e. higher hydrocarbons, non-$CO_x$).

$O_2$ conversion: the percentage of oxygen atoms in the feed converted to other products.

$MgMn_2O_4$ was prepared by solid state reaction of the component metal oxides. The lithium-modified materials based on this spinel were prepared by including a small portion of $LiOAc\cdot2H_2O$ substituted for an equimolar quantity of MgO. $CaMn_2O_4$ was prepared by solid state reaction of $CaCO_3$ with $Mn_2O_3$ Sodium-modification was effected by including portions of $NaNO_3$ in the synthesis, substituted for an equimolar amount of $CaCO_3$. In all cases the existence of the spinel phase was verified by powder X-ray diffraction.

Reactions were run in a 14mm ID X 140mm length quartz reactor; a portion of 230/325 mesh catalyst was mixed with 4g of 50 mesh quartz chips and loaded into the reactor along with additional pre- and post-beds of quartz sufficient to fill the reactor volume. Feed gases were delivered at atmospheric pressure from mass flow controllers. The temperature in the catalyst bed was measured through a quartz thermowell and ranged from 750°-760° C. The catalysts were conditioned in the reactor at 750° C. for 1 hr under $O_2$(25 cc/min) prior to starting the feed of 25 mol % $CH_4$, 5 mol % $O_2$, 70 mol % $N_2$. The feed rate per quantity of catalyst is specified by the Weight Hourly Space velocity (WHSV). This is defined as grams $CH_4$ fed to the reactor per gram catalyst per hour; the particular flows of $O_2$ and $N_2$ can be determined from the molar ratios given above. Water produced in the reaction was condensed from the effluent into a chilled trap ($-3°$ C.) and the product gas was analyzed on a Carle refinery gas analyzer. In the absence of a catalyst, there is no reaction of methane under the specified conditions.

Table I summarizes the results for the alkali-modified spinels. The results demonstrate that the $C_{2+}$ selectivity increases as a consequence of increased loadings of the alkali-modifier. Additionally, the catalysts showed no sign of aging during the 5 h period of operation, suggesting the alkali modifiers are not eluting from the spinels.

Table I provides catalytic results for cofed oxidative coupling of $CH_4$ over alkali-modified spinel catalysts. Conditions included 750° C., 1 atm; $CH_4/O_2/N_2$ volumetric ratio=5/1/14. $CH_4$ WHSV refers to grams $CH_4$ per gram catalyst per hour. Results are for about 1 hr time on stream.

TABLE I

| CATALYST | WHSV ($hr^{-1}$) | $CH_4$ CONV. | $C_2+$ SEL. | $O_2$ CONV. |
|---|---|---|---|---|
| $MgMn_2O_4$-type catalysts | | | | |
| —0.00 wt % Li | 4.92 | 8.49 | 0.0 | 81.0 |
| —0.18 wt % Li | 1.97 | 10.8 | 18.7 | 92.6 |

TABLE I-continued

| CATALYST | WHSV (hr$^{-1}$) | CH$_4$ CONV. | C$_2$$^+$ SEL. | O$_2$ CONV. |
|---|---|---|---|---|
| −0.35 wt % Li | 1.97 | 9.94 | 19.4 | 81.9 |
| CaMn$_2$O$_4$-type catalysts | | | | |
| −0.00 wt % Na | 9.84 | 11.6 | 19.9 | 91.3 |
| −0.54 wt % Na | 0.98 | 9.2 | 33.4 | 68.0 |
| −1.08 wt % Na | 0.98 | 9.6 | 47.7 | 58.6 |

As shown in Table I, the parent spinel MgMn$_2$O$_4$ exhibited no selectivity for the production of higher hydrocarbons during the oxidation of CH$_4$, yielding only combustion products CO$_2$ and H$_2$O. Catalysts with lithium-loadings of 0.18 wt % and 0.35 wt % had increased higher hydrocarbon selectivities of 18.7% and 19.4% respectively (both at 10% CH$_4$ conversion). Similarly, oxidative coupling catalyst CaMn$_2$O$_4$ gave 19.9% selectivity to ethane at 10% CH$_4$ conversion. When modified with a 0.54 wt % Na- loading, the higher hydrocarbon selectivity increased to 33.4% (9% CH$_4$ conversion). A 1.08 wt % Na-loading of CaMn$_2$O$_4$ gave a higher hydrocarbon selectivity of 47.7% (10% CH$_4$ conversion). In the latter two cases, the product included portions of ethylene along with ethane. The Examples given here were performed in a cofed mode with a feed stream containing both where CH$_4$ and oxidant (O$_2$); however, the materials might also be applied to upgrading methane in a sequential or redox mode, where separate streams of methane and oxidant are successively passed over the modified spinel to achieve the same net overall reaction.

What is claimed is:

1. A process for synthesizing one or more hydrocarbons having at least two carbon atoms by the direct partial oxidation of methane, said process comprising contacting a mixture of methane and oxygen with a spinel oxide catalyst under sufficient conversion conditions, said spinel oxide including or being combined with an alkali metal, wherein said spinel oxide is of the formula AB$_2$O$_4$, where A is Li, Mg, Na, Ca, V, Mo, Mn, Fe, Co, Ni, Cu, Zn, Ge, Cd or Sn and B is Na, Al, Ti, V, Cr, Mn, Fe, Co, Ni, Zn, Ga, Ge, Rh, Ag or In, where A and B are different elements, and wherein said conversion conditions include a temperature of from about 300° C. to about 1200° C. and a reactant partial pressure of from about 0.1 atm to about 30 atm.

2. A process according to claim 1, wherein A or B is Mn.

3. A process according to claim 1, wherein said spinel oxide is MgMn$_2$O$_4$ or CaMn$_2$O$_4$.

4. A process according to claim 1, wherein said mixture of methane and oxygen has a volume ratio of methane to oxygen of 0.1-100:1.

5. A process according to claim 1, wherein said mixture of methane and oxygen is provided by a mixture of natural gas and air.

6. A process according to claim 1, wherein said conversion conditions include a Weight Hourly Space Velocity of from 0.01 to 150 hr$^{-1}$.

7. A process according to claim 4, wherein said conversion conditions include a temperature of from 600° C. to 900° C., a reactant partial pressure of from 0.5 to 5 atm and a Weight Hourly Space Velocity of from 0.1 to 50 hr$^{-1}$.

8. A process according to claim 7, wherein said mixture of methane and oxygen has a volume ratio of methane to oxygen of 1-10:1.

9. A process according to claim 3, wherein said alkali metal is lithium.

10. A process according to claim 3, wherein said alkali metal is sodium.

* * * * *